(12) United States Patent
Hirschmann, Jr. et al.

(10) Patent No.: US 10,921,615 B2
(45) Date of Patent: Feb. 16, 2021

(54) GREY COMPOUNDED INFRARED ABSORBING SPECTACLES, GOGGLES, FACESHIELDS AND HOOD WINDOWS USED IN PERSONAL PROTECTIVE EQUIPMENT FOR ARC FLASH HAZARDS

(71) Applicants: Jack Bouton Hirschmann, Jr., South Darmouth, MA (US); Randell Bouton Hirschmann, South Dartmouth, MA (US); Thomas E. Neal, Bonita Springs, FL (US)

(72) Inventors: Jack Bouton Hirschmann, Jr., South Darmouth, MA (US); Randell Bouton Hirschmann, South Dartmouth, MA (US); Thomas E. Neal, Bonita Springs, FL (US)

(73) Assignee: Oberon Company Div Paramount Corporation, New Bedford, MA (US)

( * ) Notice: Subject to any disclaimer, the term of this patent is extended or adjusted under 35 U.S.C. 154(b) by 357 days.

(21) Appl. No.: 14/722,727

(22) Filed: May 27, 2015

(65) Prior Publication Data
US 2016/0346130 A1 Dec. 1, 2016

(51) Int. Cl.
*A61F 9/06* (2006.01)
*G02C 7/10* (2006.01)

(52) U.S. Cl.
CPC .............. *G02C 7/108* (2013.01); *A61F 9/065* (2013.01); *A61F 9/061* (2013.01)

(58) Field of Classification Search
CPC ............ A61F 9/06; A62B 17/04; G02C 7/104
USPC ............... 428/328, 458; 524/430; 250/515.1; 296/97.7; 252/500
See application file for complete search history.

(56) References Cited

U.S. PATENT DOCUMENTS

| | | |
|---|---|---|
| 2003/0054160 A1 | 3/2003 | Fisher |
| 2006/0052486 A1* | 3/2006 | Fujita ..................... C08K 9/04 523/212 |
| 2008/0075936 A1* | 3/2008 | McGurran ............ B29C 55/023 428/212 |
| 2010/0219654 A1* | 9/2010 | Fujita ................ B32B 17/10018 296/97.7 |
| 2012/0086909 A1 | 4/2012 | Paulson |
| 2014/0256865 A1 | 9/2014 | Boulton |

FOREIGN PATENT DOCUMENTS

WO 2010108975 A1 9/2010

OTHER PUBLICATIONS

Extended European Search Report and Written Opinion in EP15189837.6 dated Mar. 29, 2016.

* cited by examiner

*Primary Examiner* — Monique R Peets
(74) *Attorney, Agent, or Firm* — Vitale, Vickrey, Niro & Gasey LLP

(57) ABSTRACT

An improved personal protective device and composition thereof. The device comprises arc flash spectacles or goggles, an arc flash faceshield or an arc flash hood window to provide optical clarity, specifically color acuity. The spectacles or goggles, the faceshield and the hood window include polycarbonate material for high-impact, high-mass performance, and surface charring during arc flash exposure and provides an arc flash protective rating of at least 4 cal/cm$^2$ (in the case of eyewear and face shields) or at least 15 cal/cm$^2$ (in the case of hood windows).

2 Claims, 2 Drawing Sheets

GREY COMPOUNDED INFRARED ABSORBING SPECTACLES, GOGGLES, FACESHIELDS AND HOOD WINDOWS USED IN PERSONAL PROTECTIVE EQUIPMENT FOR ARC FLASH HAZARDS

RELATED APPLICATION DATA

This application claims priority to provisional patent application No. 61/896,751, filed on Oct. 29, 2013 and utility U.S. patent application Ser. No. 14/525,881 filed on Oct. 28, 2014.

FIELD OF INVENTION

The present invention relates to improved personal protective equipment for protecting electricians and electrical workers from arc flash exposure. In particular, the present invention is directed towards improved optically neutral spectacles, goggles, faceshields, and hood windows with a true color lens such that the user has color acuity, thus, eliminating a key potential safety hazard in the presence of energized electrical equipment with color coded electrical wiring or circuitry.

Background of the Invention

When an electric current passes through air between ungrounded conductors, or between ungrounded conductors and grounded conductors, the temperatures can reach 35,000° F. Exposure to the arc flash thermal energy from these extreme temperatures both burns the skin directly and causes ignition of conventional work clothing, which adds to the severity of burn injury. The majority of hospital admissions due to electrical accidents are from arc flash burns, not from shocks. Each year more than 2,000 people are admitted to burn centers with severe arc flash burns. Arc flash events can and do severely injure and kill workers even at distances of 10 ft (3 m).

Arc flash hazard exposure level is a function of a variety of factors, including but not limited to fault clearing time, magnitude of the arc current, the type of equipment in which the arc is initiated and a worker's distance from the arc flash event. Multiple techniques can be employed to limit risks related to such exposures. Arc flash injuries, for instance, are particularly prevalent among electricians. A myriad of solutions have been proposed to minimize such injuries.

One such method is through the use of Personal Protective Equipment (PPE) by electricians, electric utility workers and others at risk, including protective eyewear, faceshields, hoods, shirts, pants, coveralls and arc flash suits. One of the common ways to prevent eye and face injuries from an arc flash is interposing a lens or transparent window between the wearer and the arcing source. One such problem with PPE, however, is the restrictions in movement and perception which they place upon such workers. In the case of protective arc flash PPE eyewear, faceshields and hood windows, it may be essential for such workers to have full visual perception (including color acuity) in order to perceive and conduct work on energized electrical equipment as may be needed in the use of color coded electrical wiring and the like. Working on an incorrect conductor due to the worker not being able to perceive the correct color for color coded wires can be a contributing cause for an arc flash event. As a result, there is a need for arc flash PPE eyewear, faceshields and hood windows which provides optical clarity, and in particular color acuity to the user.

Description of the Prior Art

One example of a prior art approach U.S. Pat. No. 6,375,865 to Paulson purports to disclose compositions that block electric-arc energy. Specifically, Paulson claims to disclose a composition and process for manufacturing electric-arc resistant objects that are at least partially transparent. As that patent defines the term, however "substantially transparent" means a composition which allows the passage of a sufficient amount of light to allow a person looking through the material to view objects under normal working conditions. It does not, however, teach or suggest color acuity for a user. Put another way, there is a difference between transparency, i.e., being able to see objects, as opposed to color acuity, i.e., seeing objects without alteration in color versus the distortion in color perceived looking through the material used.

U.S. Pat. No. 3,382,183 to Donoian et. al. teaches a plastic optical filter related to the stabilization of infrared absorbing organic dyes in plastic substrates. A problem arises due to the degradation of the infrared dyes in sunlight and the fact that the Donoian device is simply an optical filter and not an arc shield.

A further approach is known to be offered through BSD Bildungs-und Servicezentrum GmbH. BSD has offered a Bayer Plastics product typically used in architectural or automotive applications to protect against sun light. BSD's product, however, is a faceshield with a laminate of protective film over the faceshield.

Still another publication is shown in U.S. Patent Application No. 2012/0086909 (Paulson), which discloses an arc shielding lens or a laminate for such a lens with a mixture of nanoparticles for thermal negation and absorption. However, nothing in this application teaches or suggests the need for color acuity to enable the wearer to better identify potential arc flash hazards while still being protected from an arc flash occurrence.

A further reference regarding to charring of eye and face PPE during arc flash exposure relates to polycarbonate faceshields and is described in, R. L. Doughty, Dr. T. E. Neal, T. A. Dear and A. H. Bingham, "Testing Update On Protective Clothing & Equipment For Electric Arc Exposure," IEEE Industrial Applications Magazine, Vol. 5, pp. 37-49, January/February 1999. The paper describes a reduction of arc flash thermal energy transmitted through clear polycarbonate faceshields at exposures of 21 to 25 cal/cm2 but the authors note that at the exposure level needed to generate charring, sufficient energy has already been transmitted through the faceshield to cause burn injury.

In sum, the prior art fails to teach the use of a composition for a PPE eyewear, faceshields or hood windows which enables color acuity by a wearer during use.

Definition of Terms

The following terms are used in the claims of the patent as filed and are intended to have their broadest plain and ordinary meaning consistent with the requirements of the law.

"Arc flash thermal energy" means all forms of energy created by an arc flash event including but not limited to infrared radiation, ultraviolet radiation, visible light spectrum radiation, convective energy due to hot gases and plasma, and conductive energy due to molten metal and other heated debris.

"Color acuity" means the ability to discern and distinguish between colors in the visible light spectrum.

"Eyewear" means spectacles and goggles used for protection of the eyes.

"Hood window" means a faceshield that is fitted into a hood to provide protection for the eyes, face, neck and head.

"Faceshield" means a device that protects the face and eyes and is generally attached to a hard cap or hard hat.

Eye and face PPE consists of eyewear, faceshields and hood windows.

"Optically neutral" means the near absence of any color shift in the visible light spectrum.

"Charring" means the creation of a black porous material on the surface of eye and face PPE which reduces light transmission and heat transmission through the eye and face PPE.

Where alternative meanings are possible, the broadest meaning is intended. All words used in the claims set forth below are intended to be used in the normal, customary usage of grammar and the English language.

OBJECTS AND SUMMARY OF THE INVENTION

The apparatus and method of the present invention generally include eyewear, a faceshield or a hood window for blocking or absorbing infrared radiation emanating from an arc flash event. The eyewear, faceshield and hood window are comprised of an infrared absorber including but not limited to particulates of antimony doped tin oxide, indium doped tin oxide, lanthanum boride or cesium tungstate mixed with an optically clear plastic material for providing a grey lens or shield which permits color acuity. The eyewear further includes a frame or similar support structure for the lens comprised of polycarbonate or similar non-conductive material. The faceshield is mounted on a hard cap or hard hat, and the hood window is inserted into a sewed pocket in the front of a hood and secured with a grommet or the like.

The combination of a polycarbonate optically clear plastic material and the selected particulate of the invention provides blocking of infrared radiation by the particulate at lower exposure levels that are insufficient to generate charring and provides a significantly increased level of charring which very effectively blocks higher exposure levels of arc flash thermal energy at or above the level needed to generate the charring phenomenon. In addition, the charring process removes heat from the polycarbonate lens or shield material during the formation of the char, i.e. the heated polycarbonate near the surface is removed from the surface as it undergoes pyrolysis and is converted into a thick char on the surface that very effectively blocks arc flash thermal energy. Consequently, once the charring process is initiated, the level of heat transmitted by the eye and face PPE surprisingly decreases even as the infrared radiation is increased. The concentration of particulate used in the polycarbonate optically clear plastic material must be properly set to block infrared radiation at lower exposure levels in order to avoid burn injury up to the exposure levels at which the charring process is initiated. The combination of infrared radiation blocking by the infrared absorbing particulate at low exposure levels, the removal of heat from the polycarbonate lens or shield surface and the blocking of arc flash thermal energy at higher exposure levels by the charring process permits the use of reduced levels of infrared absorbing particulate which in turn provides higher visible light transmission and consequently higher visual acuity and color acuity for the user of the eye and face PPE of this invention.

The immediate application of the present invention will be seen in providing personal protective equipment for electricians and electrical workers exposed to a wide range of arc flash conditions whereby the workers have color acuity to recognize wire color coding.

Thus it can be seen that one object of the present invention is to provide electricians and electrical workers with eyewear, faceshields or hood windows for preventing injury due to arc flash thermal energy while at the same time providing workers with color acuity in order to reduce the likelihood of working on an incorrect wire or circuit part due to color distortion.

A further object of the present invention is to provide eyewear, a faceshield and a hood window which inhibits the tinting or discoloration of objects being viewed therethrough.

Still another object of the present invention is to provide eyewear and a faceshield which can block and dissipate up to 40 cal/cm$^2$ and a hood window which can block and dissipate up to 140 cal/cm$^2$ of arc flash thermal energy.

Yet another object of the present invention is to provide eyewear, a faceshield and a hood window which includes an infrared absorber for blocking infrared radiation.

Still another object of the present invention is to provide eyewear, a faceshield and a hood window which provides an electrical worker protection from arc flash events combined with a superior ability to detect and address potential arc flash conditions over prior faceshield compositions.

Yet another object of the present invention is to provide eyewear, a faceshield and a hood window which includes a very thin gold coating on the surface to reflect radiant heat in prolonged exposures such as experienced by firefighters and some industrial workers who deal with molten metals or other molten substances. The gold coating reflects a substantial portion of the radiant heat exposure and the grey eyewear, faceshield and hood window absorbs a substantial portion of the remaining infrared radiation that is not reflected by the thin gold surface coating.

It should be noted that not every embodiment of the claimed invention will accomplish each of the objects of the invention set forth above. In addition, further objects of the invention will become apparent based the summary of the invention, the detailed description of preferred embodiments, and as illustrated in the accompanying drawings. Such objects, features, and advantages of the present invention will become more apparent in light of the following detailed description of a best mode embodiment thereof, and as illustrated in the accompanying drawings.

DETAILED DESCRIPTION OF THE INVENTION

Set forth below is a description of what is currently believed to be the preferred embodiment or best examples of the invention claimed. Future and present alternatives and modifications to this preferred embodiment are contemplated. Any alternatives or modifications which make insubstantial changes in function, in purpose, in structure or in result are intended to be covered by the claims in this patent.

Figure 1:
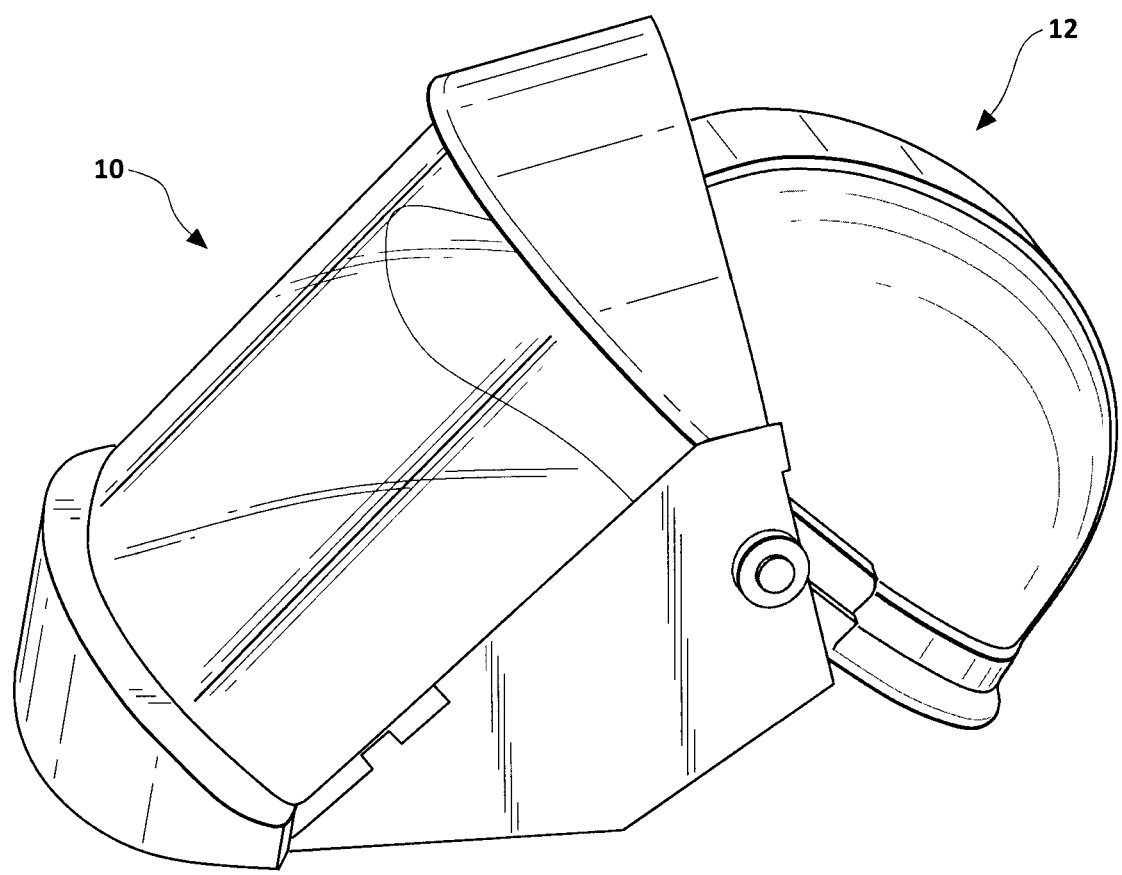
FIG. 1 shows a perspective view of a faceshield according to a first preferred embodiment of the invention.
Figure 2:
FIG. 2 shows a perspective view of a hood according to a first preferred embodiment of the invention.

FIG. 1 shows a first preferred embodiment of a faceshield 10 constructed in accordance with the present invention. The faceshield 10 is attached to a hard hat 12 or other type of headgear and protects users from electric arcs while at the same time allowing the user to view objects with color acuity. The optically clear plastic material for this product is preferably polycarbonate, but may also include acrylics, cellulose propionates, cellulose acetates and cellulose acetate butyrate or similar optically clear plastics known to those of skill in the art. Similarly, a face shield 10 in accordance with the present invention may be fitted into a hood 20 (as shown in FIG. 2), or eyewear, like spectacles or goggles may be constructed in accordance with the present invention.

In order to provide the necessary user protection for the optically neutral faceshield 10 of the present invention, the invention should further include a particulate comprised of antimony doped tin oxide particles coated with a dispersant for blocking infrared radiation associated with arc flashes and similar events. Such particulate may be of a nanoparticle size. Such a particulate for use with the present invention typically consists of nanoparticles of antimony doped tin oxide that are coated with a dispersant to provide a dispersible powder with dimensions in a range of about 5-15 microns, and most preferably about 10 microns.

A coating on substantially each antimony doped tin oxide particle is important for it to disperse in the optically clear plastic material, such coating being applied by fluidized bed, sol-gel, sputtering, evaporation or other methods known to those of skill in the art. Without the coating in the practice of the present invention, the particles are difficult to disperse evenly in the processing of the particles in mixing with the optically clear plastic material and the molding of the plastic part. In the absence of such a coating, the faceshield will have a haze that will affect the visibility through the optical part (shield or lens) and prevent or diminish the color acuity provided by the present invention.

In an attempt to quantify the advantage of the present invention, the following table compares several different models of face shields in their ability to transmit the visible light spectrum therethrough. That is, a goal of the present invention is to provide both: 1) a higher level of transmission of visible light across the visible light spectrum; and 2) a substantially consistent transmission of light across the visible light spectrum (i.e., so as to maintain color acuity). Specifically, the following comparison shows: 1) a conventional green IR arc flash shield, 2) a range of concentration of particulate plus dispersants as a weight per pound of optically clear polycarbonate material manufactured in accord with the present invention, and 3) a "clear" face shield:

| | Concentration of Antimony Doped Tin Oxide with | | | | | |
|---|---|---|---|---|---|---|
| Wavelength (nm) | .3 g Epolin 1125/lb. ClearPolycarbonate % Trans. | 5 grams/lb. Clear Polycarbonate % Trans. | 7 grams/lb. Clear Polycarbonate % Trans. | 9 grams/lb. Clear Polycarbonate % Trans. | 11 grams/lb. Clear Polycarbonate % Trans. | 0 grams/lb. Oberon Clear Polycarbonate % Trans. |
| 760 nm | 13.64% | 44.83% | 33.27% | 25.36% | 18.59% | 90.20% |
| 750 nm | 15.95% | 45.17% | 33.82% | 25.62% | 18.96% | 90.02% |
| 740 nm | 18.42% | 45.19% | 34.21% | 26.07% | 19.59% | 90.07% |
| 730 nm | 21.01% | 46.21% | 35.32% | 27.22% | 20.58% | 90.09% |
| 720 nm | 23.65% | 47.77% | 36.32% | 28.40% | 21.37% | 90.04% |
| 710 nm | 26.19% | 48.10% | 36.75% | 28.84% | 21.85% | 89.97% |
| 700 nm | 28.67% | 48.03% | 37.66% | 29.17% | 22.60% | 89.95% |
| 690 nm | 31.00% | 49.40% | 38.54% | 30.40% | 23.63% | 89.98% |
| 680 nm | 33.09% | 50.67% | 39.20% | 31.58% | 24.24% | 89.82% |
| 670 nm | 34.96% | 50.41% | 40.07% | 31.75% | 24.81% | 89.59% |
| 660 nm | 36.62% | 51.15% | 40.73% | 32.47% | 25.88% | 89.20% |
| 650 nm | 38.09% | 52.97% | 41.96% | 34.13% | 26.79% | 88.61% |
| 640 nm | 39.41% | 53.03% | 42.50% | 34.66% | 27.35% | 87.93% |
| 630 nm | 40.90% | 53.40% | 43.32% | 34.93% | 28.32% | 87.62% |
| 620 nm | 42.53% | 54.85% | 44.21% | 36.48% | 29.19% | 87.70% |
| 610 nm | 44.21% | 54.78% | 44.65% | 36.96% | 29.62% | 87.67% |
| 600 nm | 45.82% | 55.43% | 45.43% | 37.16% | 30.58% | 87.37% |
| 590 nm | 47.42% | 56.24% | 46.13% | 38.70% | 31.29% | 86.95% |
| 580 nm | 49.17% | 56.49% | 46.65% | 38.93% | 31.83% | 86.91% |
| 570 nm | 50.96% | 57.32% | 47.51% | 39.49% | 32.83% | 87.07% |
| 560 nm | 52.65% | 57.46% | 47.80% | 40.74% | 33.09% | 87.22% |
| 550 nm | 54.07% | 58.42% | 48.62% | 40.42% | 34.03% | 87.25% |
| 540 nm | 55.20% | 58.25% | 48.93% | 41.91% | 34.28% | 87.30% |
| 530 nm | 55.63% | 59.37% | 49.37% | 41.50% | 34.96% | 87.46% |
| 520 nm | 54.08% | 58.89% | 49.87% | 42.56% | 35.13% | 87.61% |
| 510 nm | 47.60% | 60.03% | 49.98% | 42.25% | 35.61% | 87.69% |
| 500 nm | 33.63% | 59.34% | 50.18% | 42.96% | 35.43% | 87.64% |
| 490 nm | 17.47% | 60.00% | 50.14% | 42.28% | 35.76% | 87.67% |
| 480 nm | 7.97% | 59.47% | 49.93% | 42.81% | 35.13% | 87.59% |
| 470 nm | 4.22% | 59.07% | 49.51% | 41.47% | 34.91% | 87.44% |
| 460 nm | 2.37% | 58.91% | 48.80% | 41.64% | 34.27% | 87.23% |
| 450 nm | 1.31% | 57.91% | 48.09% | 40.37% | 33.12% | 87.00% |
| 440 nm | 0.82% | 57.05% | 47.07% | 38.94% | 32.11% | 86.64% |
| 430 nm | 0.62% | 55.94% | 45.67% | 38.19% | 30.82% | 86.25% |
| 420 nm | 0.50% | 54.65% | 44.04% | 36.29% | 28.99% | 85.81% |
| 410 nm | 0.45% | 52.89% | 41.99% | 33.67% | 26.74% | 85.30% |
| 400 nm | 0.46% | 50.50% | 39.35% | 31.06% | 24.12% | 84.55% |

The range of concentrations of antimony doped tin oxide with dispersant in accord with the present invention as shown in this table correlates with the arc protective limits of the resulting product. As this chart shows, faceshields of the present invention provide substantially consistent light transmission across the visible light spectrum which results in color acuity for the user of such faceshields. Indeed, the present invention provides a higher degree of light transmission at every visible wavelength versus the example prior art "green" shield, which essentially blocks shorter wavelength visible light (i.e., in the blue-violet range) and therefore lacks the desired color acuity for use by electricians and electrical workers. Furthermore, while the example faceshield in accord with the present invention does not have the same level of light transmission as a "clear" faceshield, the present invention, unlike the clear shield, has infrared radiation absorption properties that enable its use in hazardous environments having the potential for arc flash events. For instance, the invention in the form of a faceshield and in the form of a hood window has been subjected to arc testing according to the American Society of Testing and Materials Test Method F2178. This test method is used to quantify the level of protection provided by arc resistant eyewear, faceshields and hoods. This test provides an arc rating value for face and head protective equipment such as eyewear, faceshields and hoods equipped with hood windows, which, in the case of the faceshields manufactured in accord with the present invention have arc ratings of 4 to 40 cal/cm$^2$, and in the case of hoods equipped with hood windows manufactured in accord with the present invention have an arc rating of 15 to 140 cal/cm$^2$. The faceshields and hoods equipped with hood windows that were tested also meet the requirements of the National Fire Protection Association standard 70E. The faceshield 10 can further optionally include a very thin gold coating on its surface to reflect radiant heat in prolonged environmental exposures, such as experienced by firefighters, smelters and the like. The gold coating reflects a substantial portion of the radiant heat exposure and the grey eyewear, faceshield and hood window absorb a significant portion of the remaining infrared radiation that is not reflected by the thin gold surface coating. As a further option, the faceshield may have added to it selected amounts of a dye of a color within the visible light spectrum. Thus, unlike traditional green or orange tinted-faceshields, the present invention creates a medium-density filter allowing visibility across the visible light spectrum that also allows color acuity. Furthermore, for increased ultraviolet radiation protection, it may be desirable to add up to 1% by weight of an ultraviolet radiation absorbing compound to the eyewear, faceshield and hood window compositions.

The above description is not intended to limit the meaning of the words used in the following claims that define the invention. Rather, it is contemplated that future modifications in structure, function or result will exist that are not substantial changes and that all such insubstantial changes in what is claimed are intended to be covered by the claims. For instance, those of skill will understand that the instance invention can also apply to other forms eyewear beside spectacles, goggles, faceshields and hood windows. Likewise, it will be appreciated by those skilled in the art that various changes, additions, omissions, and modifications can be made to the illustrated embodiments without departing from the spirit of the present invention. All such modifications and changes are intended to be covered by the following claims.

We claim:

1. A faceshield for blocking arc flash thermal energy including infrared energy, the faceshield comprising:
   a lens providing color acuity within the visible light spectrum, wherein the lens provides at least 44% light transmission across the visible light spectrum, the lens comprised of antimony doped particulate that blocks infrared radiation, and an optically clear plastic material, the optically clear plastic material and the particulate chosen and blended in proportion so that the faceshield will block a range from 3 to 40 cal/cm$^2$ of arc flash thermal energy, the lens further comprising of:
   a) an optically clear plastic material selected from the group consisting of but not limited to polycarbonate, acrylic, cellulose propionate, cellulose acetate and cellulose acetate butyrate; and
   b) a particulate consisting essentially of an antimony doped tin oxide coated with a dispersant wherein the antimony doped tin oxide coated with a dispersant has a size range of about 5 to 15 microns per particle; and
   c) the particulate described in b) dispersed within said optically clear plastic material.

2. The faceshield of claim 1, wherein the lens is optically neutral and provides at least 44% light transmission across at least a portion of the visible light spectrum including a range from about 430 nm to about 590 nm.

* * * * *